United States Patent
Friemel et al.

(12) 
(10) Patent No.: US 6,537,220 B1
(45) Date of Patent: Mar. 25, 2003

(54) ULTRASOUND IMAGING WITH ACQUISITION OF IMAGING DATA IN PERPENDICULAR SCAN PLANES

(75) Inventors: Barry Hugh Friemel, Redmond, WA (US); Charles Dale Emery, Issaquah, WA (US)

(73) Assignee: Siemens Medical Solutions USA, Inc., Iselin, NJ (US)

( * ) Notice: Subject to any disclaimer, the term of this patent is extended or adjusted under 35 U.S.C. 154(b) by 0 days.

(21) Appl. No.: 09/944,650

(22) Filed: Aug. 31, 2001

(51) Int. Cl.[7] .................................................. A61B 8/00
(52) U.S. Cl. ....................................... 600/447; 600/459
(58) Field of Search ................................. 600/437, 443, 600/447, 459; 128/916

(56) References Cited

U.S. PATENT DOCUMENTS

| | | | | |
|---|---|---|---|---|
| 4,794,929 A | * | 1/1989 | Maerfeld | 73/625 |
| 4,870,867 A | * | 10/1989 | Shaulov | 73/625 |
| 5,103,129 A | * | 4/1992 | Slayton et al. | 310/335 |
| 5,797,845 A | * | 8/1998 | Barabash et al. | 600/443 |
| 5,901,708 A | * | 5/1999 | Chang et al. | 128/916 |
| 6,123,669 A | * | 9/2000 | Kanda | 600/443 |
| 6,276,211 B1 | * | 8/2001 | Smith | 600/447 |
| 6,279,399 B1 | * | 8/2001 | Holm | 73/626 |
| 6,352,510 B1 | * | 3/2002 | Barabash et al. | 600/443 |
| 2002/0035328 A1 | * | 3/2002 | Roundhill et al. | 600/443 |

OTHER PUBLICATIONS

Snyder, et al., "Real–Time Orthogonal Mode Scanninng of the Heart. I. System Design," Journal of the American College of Cardiology, vol. 7, No. 6, pp. 1279–1285, Jun. 1986.

* cited by examiner

*Primary Examiner*—Francis J. Jaworski

(57) ABSTRACT

An ultrasonic imaging array has two independent, interleaved linear subarrays occupying a common array face. The subarrays are independently steerable and focusable in different imaging planes. The subelements making up the elements in of the subarrays is preferably quadrilateral. Adjacent subelements in each element are electrically connected via an interconnect portion such that the interconnect portion connecting each pair of adjacent subelements in each element is substantially linear and is aligned with the diagonals of the adjacent subelements. A preferred acoustic lens is curved in both azimuth and elevation directions, whereby the subarrays are independently focusable. By transmitting in one plane and simultaneously receiving in a different, orthogonal plane, a system including the array can image a 3-D region of interest (ROI). In a volumetric embodiment of the invention two orthogonal B-mode images of a structure within the ROI are displayed simultaneously. The user may then trace the outlines of the images and the system therefrom calculates the volume of the structure.

20 Claims, 11 Drawing Sheets

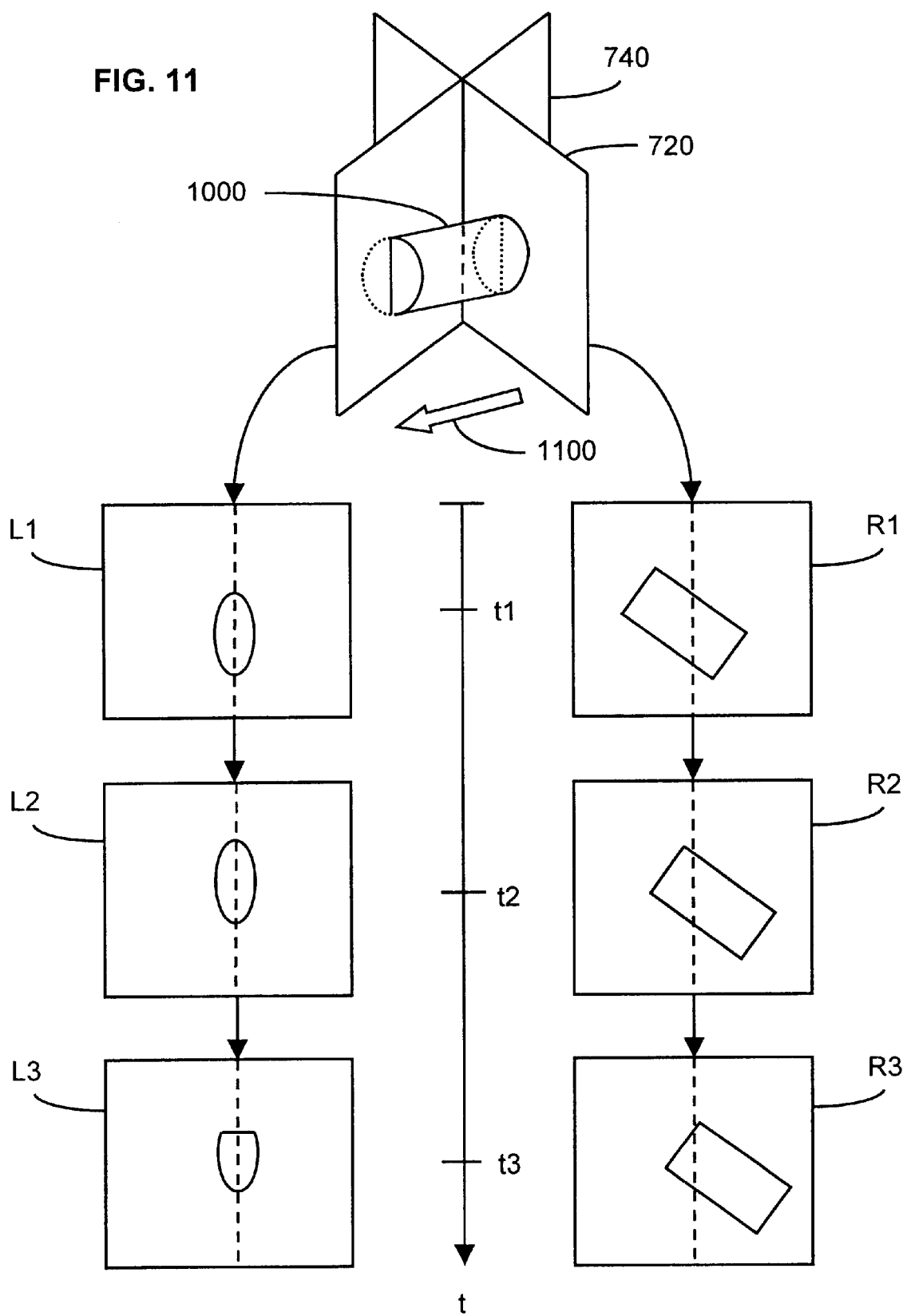

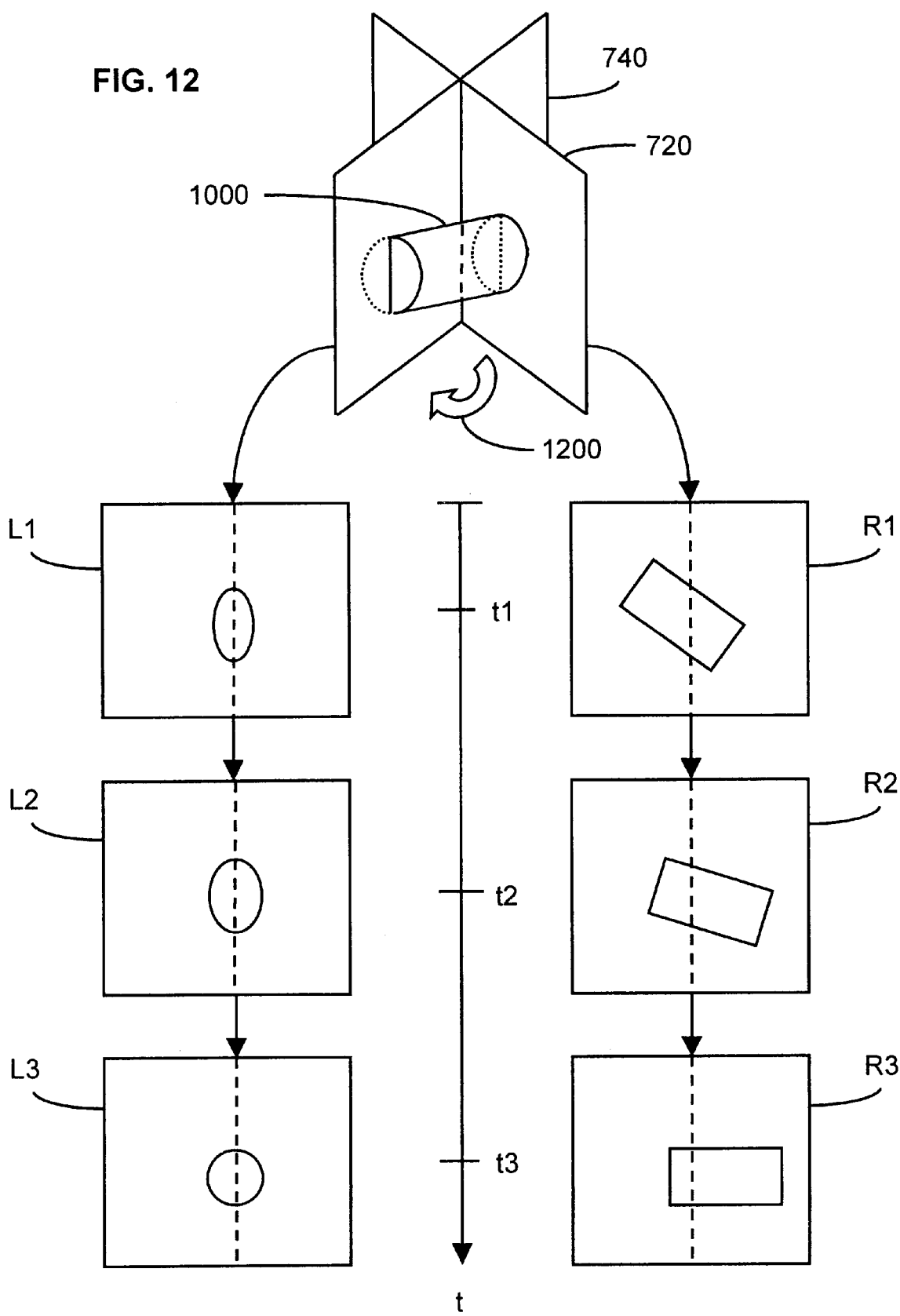

ULTRASOUND IMAGING WITH ACQUISITION OF IMAGING DATA IN PERPENDICULAR SCAN PLANES

BACKGROUND OF THE INVENTION

1. Field of the Invention

This invention relates in general to an ultrasound transducer that has a two-dimensional (2-D) array of transducer elements, and in particular to a 2-D transducer array for acquiring imaging data in different scan planes.

2. Description of the Related Art

The value of ultrasonic imaging as a diagnostic tool is undisputed, and as the power of ultrasound imaging systems increases, so too do the number of applications of the technology. Examples of such applications include the determination of the size and location of tumors and arterial occlusions. Another application that shows growing promise is in the area of cardiac imaging. As in many areas of diagnostics, however, physicians (and of course, patients themselves) prefer minimally, or, ideally, completely non-invasive techniques. This reduces the desirability of intracardiac imaging transducers, which are carried at the end of a catheter that is threaded into the heart via a major vein in the arm, neck or groin. There are, accordingly, several known systems in which both specialized and multi-purpose ultrasound systems are used for cardiac imaging via an externally applied probe.

One requirement that restricts the use of general ultrasound transducers is that some cardiac exams need the acquisition of two views from a common window. These views (two-chamber, four-chamber or short/long axis) are often approximately perpendicular to one another, which means that the operator must twist the probe in order to acquire both views. For example, multi-planar ultrasound scans are found in some systems used to determine cardiac output.

One way to achieve a display of real-time imaging planes, as well as calculate cardiac output reliably, is to design and use a 3-D ultrasound scanner. Unfortunately, the complexity and cost of such a real-time 3-D (sometimes referred to as 4-D) system are formidable. For example, a 2-D array is commonly used to interrogate the volume in real-time. Unfortunately, the element count for such a 2-D array is usually much larger (typically, well over 4000 elements) than for a 64-element 1-D array in order to achieve the same imaging performance.

To circumvent this problem, most existing real-time 3-D systems use a sparsely sampled aperture, which reduces not only the signal-to-noise ratio (SNR) of the transducer, but also the contrast and detail resolution relative to what a linear array can achieve. The transducer's performance can be improved by using a complex multilayer ceramic array in transmit and receive, a receive preamplifier in the transducer assembly and/or more transducer elements. Even with these techniques, a sparsely sampled aperture still requires a significant number of elements, typically at least ten times greater than a conventional 64-element array. Because of the large number of elements that must be addressed in a sparse 2-D array, multiplexing (synthetic aperture) is sometimes used, but this reduces the frame rate.

What is needed is an ultrasound probe that is able to offer 3-D, real-time imaging information, that can shorten examination time, and that avoids the complexities found in a conventional real-time 3-D scanner. The probe should use a common array face in order to maintain a small footprint, which is particularly important for cardiac applications. Moreover, the probe should have contrast and detail resolution comparable to what can be achieved using a linear array. This invention provides such a probe.

SUMMARY OF THE INVENTION

An ultrasonic imaging array according to the invention comprises two independent, interleaved linear subarrays that occupy a common array face. The subarrays are independently steerable and focusable in different imaging planes. One advantage of the preferably embodiment of the array according to the invention is that each subarray is able to form an independent, unswitched aperture.

In the preferred embodiment of the invention, each subarray comprises a plurality of elements and each element comprises at least one subelement. Each subelement is quadrilateral and has a diagonal and adjacent subelements in each element are electrically connected via an interconnect portion. The interconnect. portion that connects each pair of adjacent subelements in each element is preferably substantially linear and is aligned with the diagonals of the adjacent subelements. In the preferred embodiment of the invention, the diagonals of all subelements in each element are aligned and the interconnect electrically connecting the subelements in each element is linear over the extent of the array A multi-layer flex circuit is preferably used to connect the various element "interconnects to the external control and processing system. In this case, the interconnects for a first one of the subarrays are patterned as first linear traces onto a first separate layer of the flex circuit and extend to a first edge of the array face. The interconnects for a second one of the subarrays are then patterned as second linear traces onto a second separate layer of the flex circuit and extend to a second edge of the array face that is different from the first edge. A connector may then be provided for each subarray, the connector for each subarray being connected to the interconnects of the respective subarray along the respective edge.

The invention also allows the array to be connected in a multidimensional configuration such as, for example, 1.5 D or 1.75. The subelements in each element are in such embodiments grouped into a plurality of groups, the groups in each element of each respective subarray having the same relative position within the subarray. The subelements in each group are then electrically connected, whereby each subarray operates as a multidimensional array, with a dimension greater than one and less than two. For example, a first group may consist of a central plurality of subelements and a second group may consist of the plurality of subelements located on either side of the first group.

The array preferably comprises first and second subelements, in which the first subelements comprise a first one of the subarrays; the second subelements comprise a second one of the subarrays; edges of the subelements extend in a first and a second direction; and the first and second subelements are arranged in a pattern in which they alternate in both the first and second directions.

The invention also provides an acoustic lens mounted over the array face, which defines a single, common aperture, in which each subarray comprises a plurality of elements, the elements in a first one of the subarrays extend in an azimuth direction, and the elements in a second one of the subarrays extend in an elevation direction, which is orthogonal to the azimuth direction. The lens is preferably curved in both the azimuth and elevation directions, which allows the subarrays to be independently focusable.

Instead of using the lens, the subelements may be diced from ceramic so as to be convex-concave", that is, curved in both the first and second dimensions, the first and second directions being orthogonal, whereby the subarrays may be focused in both the first and second directions.

Because the subarrays according to the invention may be controlled independently, they may be operated so as to generate simultaneous transmit beams and/or receive simultaneous echo signals within the region of interest along the different imaging planes. In embodiments of the invention in which dual transmit beams are generated, the transmit beams may have different waveforms. It is also possible according to the invention to generate a transmit beam in one imaging plane and receive from the orthogonal plane; indeed, this method is used in one embodiment of the invention that makes possible 3-D imaging from within an entire volume of interest.

The invention is also able to generate from the received echo signals and simultaneously display for a user two orthogonal cross-sectional B-mode images of the region of interest. In this case, where the region of interest includes a body structure, the invention also comprises a method in which the user moves the array to a plurality of positions and, at each position, traces a periphery of the body structure as displayed in a first one of the orthogonal cross-sectional B-mode images. A system according to the invention then measures the distance of movement of the array as a function of sequentially generated second ones of the B-mode images, which are orthogonal to the first B-mode images. It then also calculates a volume of the structure as a function of the products of areas within the traced periphery and the corresponding measured distances, summed over all the positions of the array.

BRIEF DESCRIPTION OF THE DRAWINGS

FIG. 11 shows how the simultaneous images of the 3-D object changes as the probe in which the array is mounted is translated, that is, moved in a given direction.

FIG. 12 shows how the simultaneous images of the 3-D object changes as the probe in which the array is mounted is rocked, i.e., rotated about a single axis.

DETAILED DESCRIPTION

Considered in broadest terms, the ultrasound transducer probe according to the invention is a fully sampled 2-D array that consists effectively of two independent perpendicular but "interleaved" linear arrays that occupy a common array face. The two "interleaved" linear arrays can be electronically steered and focused in two independent imaging planes. This unique configuration of the elements in the different embodiments of the 2-D array according to the invention allows not only for simultaneous perpendicular acquisition from a common aperture, but also efficient and symmetric electrical connections. Here, the word "simultaneous" refers to the acquisition of the two imaging planes occurs at the same time; moreover, the invention is able to accomplish this without requiring electronic switching between the apertures. In some implementations of the invention, it is also possible to activate both arrays and thereby transmit along both imaging planes at the same time, still with no need for electronic switching.

Figure 1:
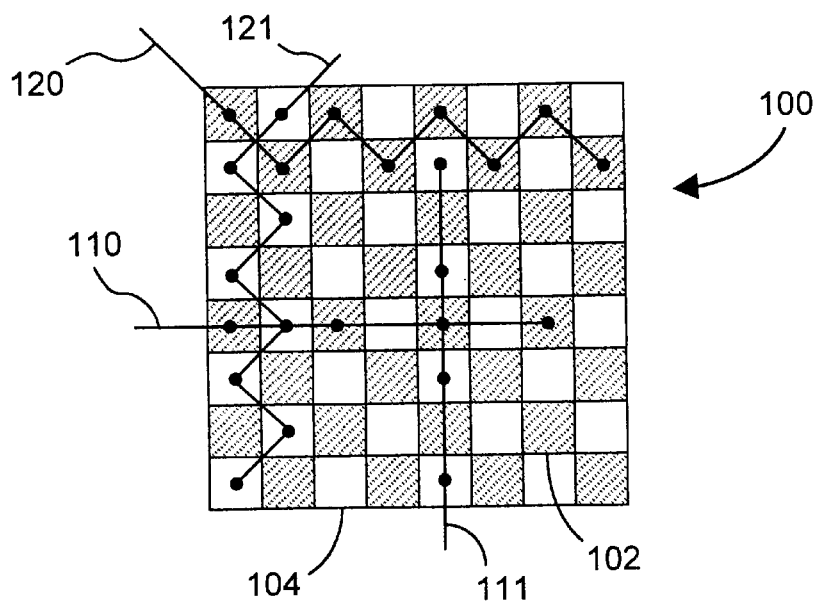
FIG. 1 illustrates the element configuration found in a 2-D transducer array according to the invention, with interconnections to create a biplane transducer.

FIG. 1 illustrates a portion of a 2-D array 100 that would enable simultaneous image acquisition along two different scan planes. In FIG. 1, the kerfs between adjacent subelements are not shown for the sake of simplicity and clarity. In this array, the subelements are divided into two groups: in FIG. 1, this is illustrated by the first group being shaded gray and the second group being unshaded.

In this description, the term "subelement" refers to the smallest, diced portion of the array that can be independently electrically activated. According to the invention, several of the subelements are electrically connected so as to be activated at the same time; each electrically connected set of subelements is an "element." The example of an array shown in FIG. 1 thus has 8×8=64 elements, where each element in turn consists of eight electrically connected subelements.

In the embodiment shown in FIG. 1, the dicing lines, for example, line 102, which define the kerfs that separate adjacent subelements, are parallel to the edges, for example, edge 104, of the array. In other words, such an array arranges the piezoelectric transducer elements in a chessboard pattern. This design has several weaknesses, among which are the increased difficulty of providing signal leads to the individual elements, even those that are to be connected to each other and/or decreased dicing pitch, which is the distance between the lines separating the elements.

For example, assume that like subelements (that is, of the shaded first group or of the unshaded second group) are to be connected row- or column-wise. Each lead, such as the conductor 110, must then "skip" every other subelement (the shaded ones) in order to connect (indicated by dots) the like subelements in the row. The unshaded subelements in each column, would also be connected, for example by connector 111 to form a second, "unshaded" element that interleaves the shaded element.

Now assume that each subelement is square and measures s units of length on each side. The effective element (made up of a group of subelements electrically connected in parallel) pitch is (s+k) length units, where k is the width of the kerf separating the elements. In this case, the design has the same element pitch as the imaging plane of the conventional array. Usually, the dicing pitch and the element pitch are the same in the conventional array unless subdicing is necessary. Because the electrical connections will have to "hop over" every other element, the interconnection scheme is greatly complicated, especially since it is necessary to maintain proper via separation.

Another method to enable the simultaneous acquisition of two imaging planes is also shown in FIG. 1. Subelements are electrically connected in a "zig-zag" pattern using a connector such as lead 120. A second element is connected using lead 121. In this case the element pitch is 2(s+k). One of its disadvantages is obvious, namely, the required dicing pitch decreases by a factor of 2 to achieve the same steering performance in the imaging plane as the conventional linear array. Furthermore, this design requires proper positioning and attachment of interconnects that follow the zig-zag pattern.

Figure 2:
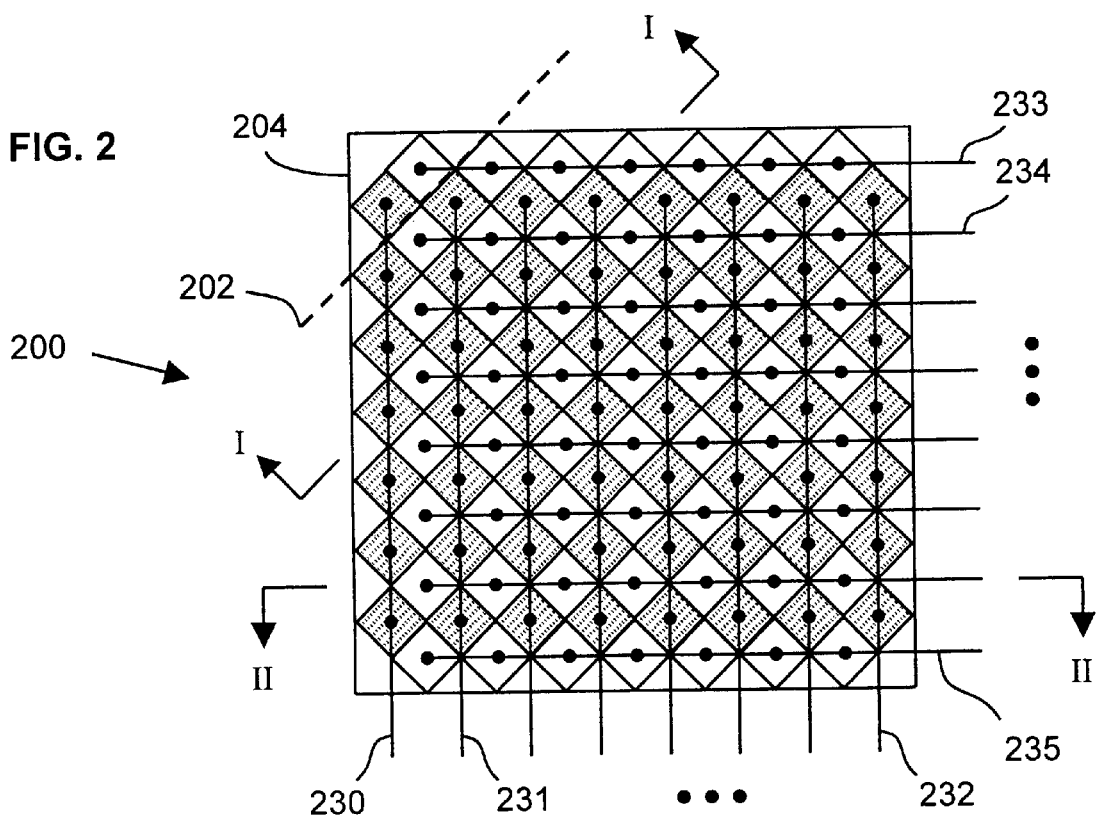
FIG. 2 illustrates the element and wiring configuration found in a first embodiment of a 2-D transducer array according to the invention.

FIG. 2 illustrates the element geometry in the preferred embodiment of the 2-D array 200 according to the invention: The piezoelectric transducer subelements (again, alternately unshaded and shaded) are arranged in a "diamond" pattern. More precisely, each of the subelements is four-sided, that is, square or at least rectangular, although it is also possible according to the invention for the elements to have the shape of equilateral or even non-equilateral parallelograms (a rhombus) or of other quadrilaterals. In the preferred embodiment, the subelements with corners that are diagonally across from each other are electrically connected. This occurs only along one direction.

In FIG. 2, the, perimeter of the active array face is shown as being rectangular; this is normal in transducer design, even though the array is often mounted in a probe head with some other shape. This rectangular configuration is not required by the invention. For example, the aperture could be circular or square, depending on the application. As is mentioned above, the elements are preferably at least approximately square, with separating kerfs, such as kerf 202. In the illustrated embodiment of the invention the kerfs 202 are at an angle of 45 degrees relative to array edge 204; other kerfs will then be either parallel to kerf 202 or perpendicular to it. This is not necessary to the invention, however, since the total shape of the array face need not even be square or rectangular.

As is also mentioned above, it is not necessary to the invention for the elements to be square. For example, different angles of separation are possible using different proportioned rectangles. As is explained below, the shaded, first subelements and the unshaded, second subelements are preferably connected by row and column, respectively, to form perpendicularly oriented linear arrays. Subelement shapes that are rectangular will cause the element pitch of adjacent, electrically connected subelements in the rows or columns to be the same. The array 200 in this preferred embodiment of the invention is then wired so as to form two interleaved sub-arrays (of shaded and unshaded "columns" and rows" of elements, respectively). Viewed and shaded as in FIG. 2, the subelements in each sub-array are then electrically connected so as to form parallel vertical columns of subelements (in FIG. 2, the shaded subelements) and parallel horizontal rows of subelements (in FIG. 2, the unshaded subelements). The shaded subelements therefore form a vertical linear array and the unshaded subelements form a horizontal linear array. Note that the interconnect for each subarray is aligned with the diagonals of each subelement; in other words, the subelements in each element are connected "corner to corner."

In FIG. 2, the electrical connectors 230, 231, . . . , 232 connect the shaded subelements in respective columns, and the electrical connectors 233, 234, . . . , 235 connect the unshaded subelements in respective rows. Again, the dots on the illustrated connectors indicate conventional electrical connections with the respective PZT subelements.

In operation, all of the subelements in any given row or column are energized at the same time (since they are electrically connected), so that each row and each column forms a separate signal channel. Thus, a 64-by-64 array of subelements would have 64+64=128 separate channels or elements, whose signals are processed in the conventional manner by the external processing system to which the transducer array is connected.

Even at this point, one advantage of the invention can be seen: As with the "zig-zag" interconnection scheme, the effective element pitch is only sqrt(2)*(s+k) length units, assuming as before that the subelements are s length units per side; however, with this embodiment of the invention, straight interconnects can be used to connect the subelements. The dicing pitch required to maintain the same imaging performance as the conventional array decreases by sqrt(2).

In the embodiment of the invention illustrated in FIG. 2, each element contains the same number of subelements, although it is of course possible using the invention to have more elements in the horizontal array than in the vertical, if for some reason this is desired. Furthermore, each element in the horizontal array may have more or fewer subelements than the vertical array. Finally, it is also possible for the elements within either the horizontal or vertical array to have different amounts of subelements (FIG. 8).

Figure 8:
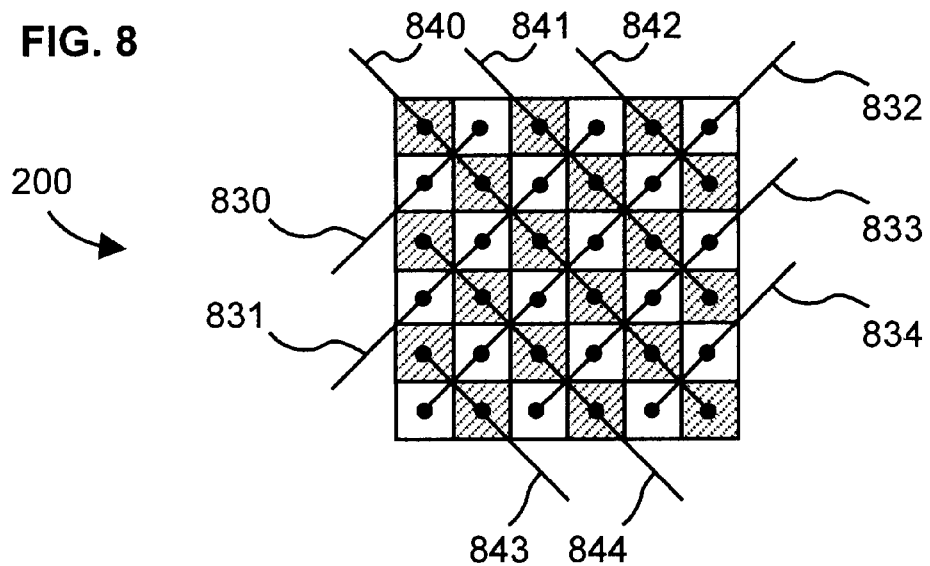
FIG. 8 illustrates an alternative interconnection arrangement for the elements in the 2-D array according to the invention.

FIG. 8 illustrates an alternative interconnection arrangement for the elements in the array 200. For the sake of simplicity, only a portion of the elements of the array is shown. In this arrangement, the subelements are four-sided, here, square, with edges that are parallel to the edges of the array as a whole. As before, the interconnects that connect adjacent subelements in each row are aligned with the diagonals of the subelements. Thus, interconnects 830–834 connect adjacent "diagonals" (each an element) of unshaded subelements and interconnects 840–844 connect shaded subelements.

Note that in the arrangement shown in FIG. 8 there are different numbers of subelements in different portions of the array. Thus, there are only two subelements in the corner element that is controlled via conductor 843, whereas there are five subelements in the element connected by connector 840. An advantage of the embodiment shown in FIG. 8 is that it provides apodization; a disadvantage, however, is that all of the connectors in each sub-array do not terminate along the same edge of the array. Thus, interconnects 830 and 831 extend out from a different edge than interconnects 832, 833, 834.

Figure 3:
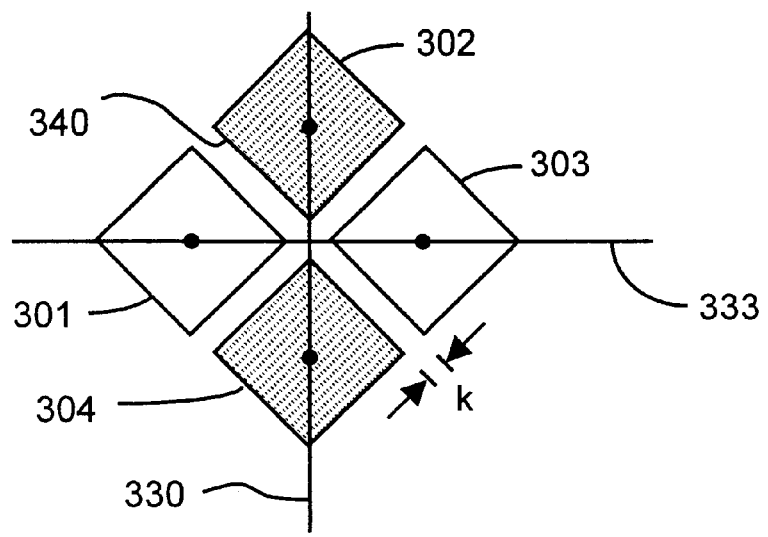
FIG. 3 shows, on a greatly enlarged scale, several array elements from the first embodiment of the invention, as well as the kerfs between them.

FIG. 3 illustrates in greater detail the subelement geometry for the preferred embodiment of the invention. FIG. 3 shows a four-element portion of the array: Horizontal (unshaded) array subelements 301, 303 are connected by interconnect 333, and vertical (shaded) array subelements 302, 304 are connected by interconnect 330. Each adjacent pair of electrically connected subelements in the illustrated, first embodiment of the array is separated by a kerf 340 of width k. The distance, between adjacent electrically connected subelements, such as between subelements 302 and 304 or between 301 and 303, will then be P=(s+k)*sqrt(2), where s is the length of a side of each subelement.

One advantage of the illustrated geometry and the aligned-diagonal interconnect scheme is that is reduces the cross talk between transmit apertures by maximizing the distance between the subelements. To avoid grating lobes in the two perpendicular scan planes generated by the different arrays (with shaded and unshaded subelements, respectively) of interest, the effective element pitch should not exceed $\lambda/2$, where $\lambda$ is the wavelength of the highest frequency of interest.

Figure 4:
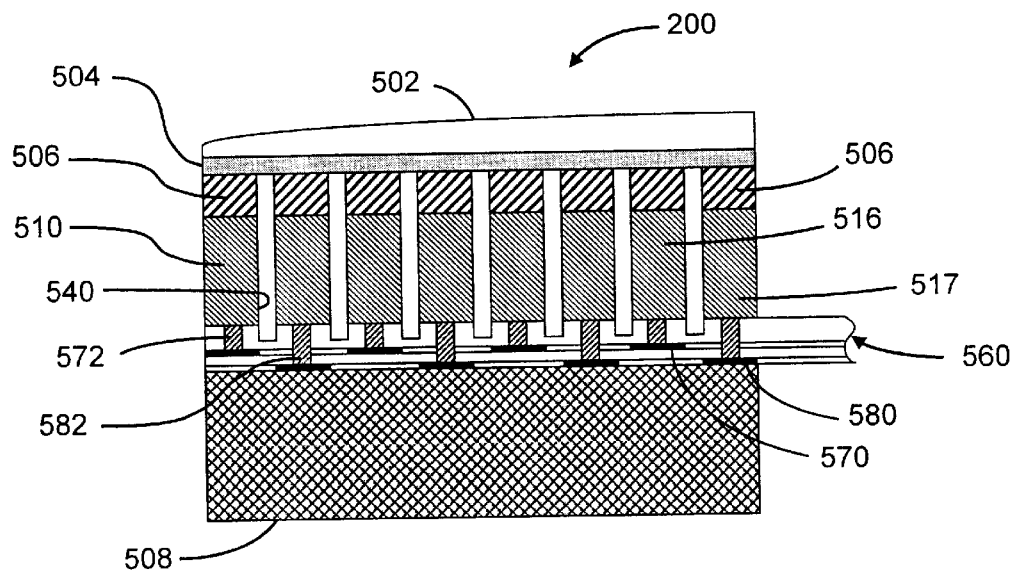
FIGS. 4 and 5 are cross-sectional views of the preferred embodiment of the array taken along lines I—I and II—II, respectively, in FIG. 2.

FIG. 4 is a cross-sectional view through a portion of the array 200 covering eight laterally adjacent subelements, for example, taken along view line I—I in FIG. 2. (Note that the two 8-by-8 subelement arrays shown in FIG. 2 will normally be only a portion of the actual array, with the rest of the array having the same structure.) The probe includes conventional structures, such as an acoustic lens 502, and matching layers 504 and 506, which may (but need not be) diced along with the subelements. The array is mounted on a conventional backing layer 508.

The subelements 510, . . . , 516, 517 themselves are, as in conventional probes, manufactured from a piezoelectric (PZT) material and are separated using conventional dicing by kerfs 540. Of course, other active devices or materials such as CMUT's (capacitive micromachined ultrasonic transducers) could also be used to build such a geometry. In the preferred embodiment of the invention, electrical signals to and from the different subelements are led via conductive traces patterned onto or otherwise included in a multi-layer flex circuit 560. Such flex circuits, and their manufacture, are described, for example, in U.S. Pat. No. 5,617,865 (Palczewska, et. al., "Multi-dimensional ultrasonic array interconnect, issued Apr. 8, 1997), and U.S. Pat. No. 5,920,972 (Palczewska, et. al., "Interconnection method for a multilayer transducer array," issued Jul. 13, 1999).

Assume by way of example that every other subelement in FIG. 4, starting with the leftmost subelement 510 corresponds to a shaded subelement in FIG. 2, and that the remaining subelements (such as 517) correspond to unshaded subelements. Each subelement must of course be connected electrically to the external processing system (not shown). The shaded (first) subelements are connected by means of conventional vias 572 to electrodes on first traces 570, which will, in this example, be bussed perpendicularly out of the plane of the figure. Similarly, the unshaded (second) subelements are connected by means of conventional vias 582 to electrodes on second traces 580, which will, in this example, be bussed in the plane of the figure.

Figure 5:
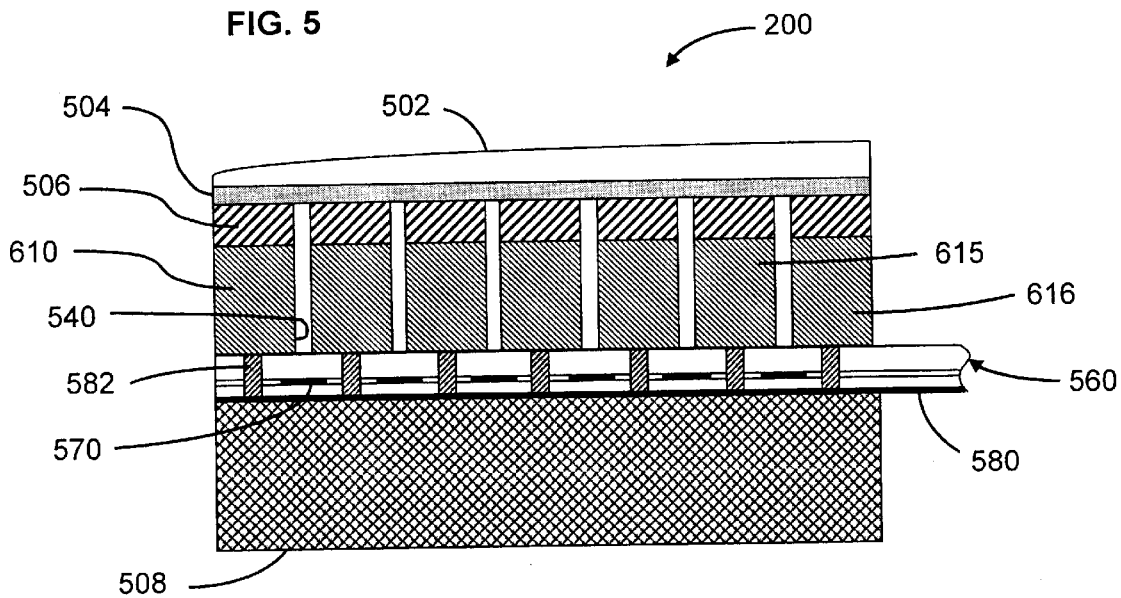

FIG. 5 is a cross-sectional view of a portion of the array 200 taken along To line II—II in FIG. 2, that is, through one row (or at least part of a row) of second (unshaded in FIG. 2) subelements 610, . . . , 615, 616. Other parts of the array are numbered as in FIG. 4. Note how the single, straight trace 580 is able to connect all the subelements in the row.

Depending on the type of flex circuit used in any given application, it may be possible to eliminate the first vias 572 and arrange the electrodes and first traces for the shaded, first subelements directly on the upper surface of the flex circuit 560. One must then make sure to lead the traces 570 so as to avoid electrical contact with the second (unshaded) subelements. Another possibility is using a flex circuit on the top and bottom of the array. For example, column-wise subelements would be connected on the top of the array and row-wise subelements would be connected on the bottom of the array. This may reduce electrical crosstalk.

Conventional design methods may be used to fashion such a flex circuit. It is, moreover, not necessary to use a flex circuit at all in order to provide the electrical connections between the various subelements and the external processing circuitry; rather, other conventional interconnection devices and arrangements may be used. For example, patterning the PZT on both sides using photolithography, or wire bonding could instead be used to make the electrical connections. CMUT's may even make the interconnection easier because of the ability to produce patterned interconnects on silicon. The invention does not depend on any particular type of interconnection arrangement. The use of a flex circuit is, however, advantageous for reasons that are well known in the field of transducer design. Unique to this invention, however, is that the arrangement of subelements into perpendicular horizontal and vertical arrays allows for the traces of the horizontal sub-array to be led in parallel traces to one edge of the array 200, with the traces of the vertical sub-array led in parallel to a different edge of the array.

Figure 6:
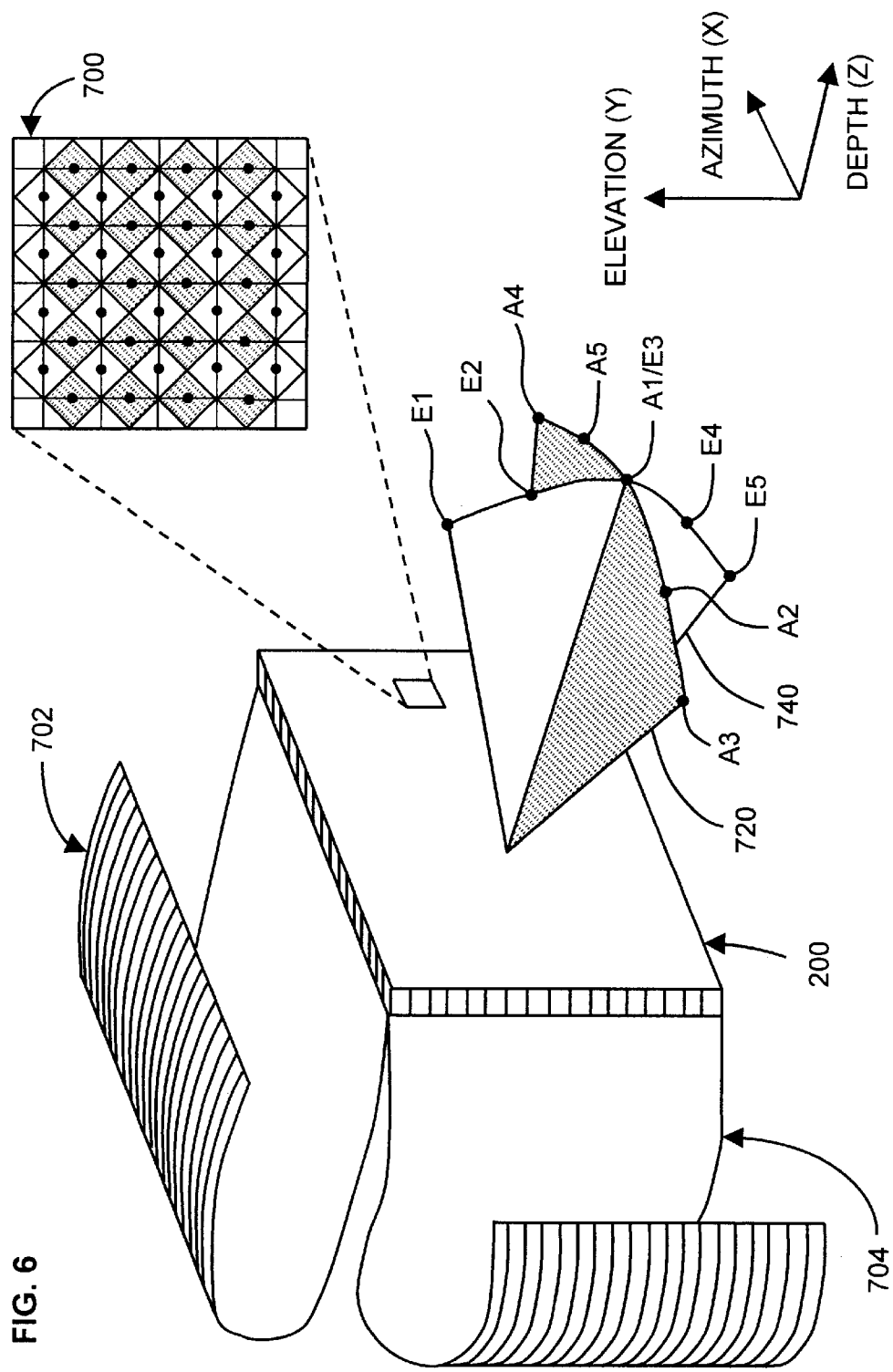
FIG. 6 illustrates not only the scan beams, but also the preferred way in which flex cables are connected to the array in order to carry signals to and from the array elements.

FIG. 6 illustrates not only the perpendicular scan planes 720, 740 (azimuthal and elevational, respectively) provided by the invention, but also the way in which conventional flex cables 702, 704 can be led to different edges of the array 200. Conductors in each flex cable will be connected in any known manner to the traces of the corresponding flex circuit, which means that each flex cable connects the external processing system (not shown) to one of the two different linear arrays (one with the first elements, the other with the second elements). FIG. 6 also shows how each portion 700 of the array 200 has the element configuration shown in FIG. 2.

Because only half of the cumulative surface area of the aperture of the array 200 is used for each imaging plane 720, 740, one would expect a loss in sensitivity. However, certain features of the invention actually help to reduce this loss of signal sensitivity. First, the smaller 2-D array elements (in "bar mode," with the thickness of the element, for example, twice the length of the sides) have a higher coupling coefficient when compared to linear array elements (which use "beam mode," where the thickness of the element is usually twice the width and the element length is much larger than the thickness). This tends to increase the pulse-echo sensitivity. Second, the array is preferably diced into a 1–3 composite, which offers a better acoustic impedance match to the body. This in turn increases element bandwidth and 'sensitivity.

Second, the preferred embodiment of the invention is able to generate simultaneous perpendicular imaging planes with no need for the space-consuming multiplexers that are required by prior art 2-D arrays used to operate with different imaging planes. This means that there will in most applications be enough room in the transducer body, which houses the array, to also include pre-amplifiers. These pre-amplifiers, which could be mounted in the transducer body, could then be connected in any known manner to pre-amplify the return signals generated by each array channel and thereby increase the received signal-to-noise ratio. A great advantage of the invention is that each of the two interleaved sub-arrays can be steered independently using conventional phasing techniques. This is illustrated in FIG. 6, along with other advantages of the invention.

In the preferred embodiment of the invention, the array subelements are aligned such that their edges are parallel with the edges of the array 200 as a whole (which may also have some edge region surrounding the active array elements). A sub-section 700 of the array 200 is shown to illustrate the general preferred element configuration. It is then possible to connect all of the subelements in each respective sub-array with a single flat multi-connector, such as a flex cable 702, 704. There is no need for complicated routing of connectors to the end subelements of the respective sub-arrays, since these will be in a line. Moreover, the cables 702, 704 can be attached to the array 200 on respective edges, with no need for them to cross each other; this makes it easier to assemble the array.

In FIG. 6, the two simultaneous imaging planes made possible by the invention are shown as the azimuth plane 720 and the elevation plane 740. The planes represent the regions within which azimuth and elevation beams can be steered using conventional phasing techniques. Thus, to image the plane 720, the azimuth beam (plane) may be moved (focused) from point A1, to A2, to A3, then wrapped around (a common scanning technique) to A4 at the other side of the plane, to A5, then back to A1. Similarly, the elevation beam may be moved in the plane 740 from E1, to E2, to E3, to E4, and to E5.

Of course, conventional transmit control techniques may be used to change the focal depth of the different subarrays. By selecting the same depth of focus for the beams in the azimuth and elevation direction, by varying the focal depth, and by scanning using the two simultaneous, orthogonal imaging planes as FIG. 6 shows, the point of focus can be moved throughout an entire 3-D volume of a region of interest.

Recall that the array according to the invention actually provides two, orthogonal, interleaved sub-arrays formed by the shaded and unshaded elements (as illustrated in the figures). Each sub-array constitutes a separate aperture, and there is no need to implement a switch between the two. The array according to the invention can then be used to provide 3D imaging by using one aperture for transmit and the orthogonal aperture for receive.

The ability of the array according to the invention to perform 3D imaging is based on the width of the beam profile in elevation away from the acoustic focus. As is well understood, away from the acoustic focus, the width of the beam is large. For example, tests on a conventional phased array for adult cardiology with beam characteristics similar to those that can be created using the invention, have shown that at a depth of 20 mm the −6 dB beam width in elevation is about 6.6 mm, whereas at a depth of 60 mm the −6 dB beam width is only 3 mm. In the azimuth dimension (imaging plane), the beam width may be electronically controlled using conventional techniques. Usually, the azimuthal beam width at all depths is much narrower than the −6 dB beam width in elevation. For example, at 20 mm the beam width is 0.7 mm and at 60 mm the beam width is 1.75 mm.

Figure 7:
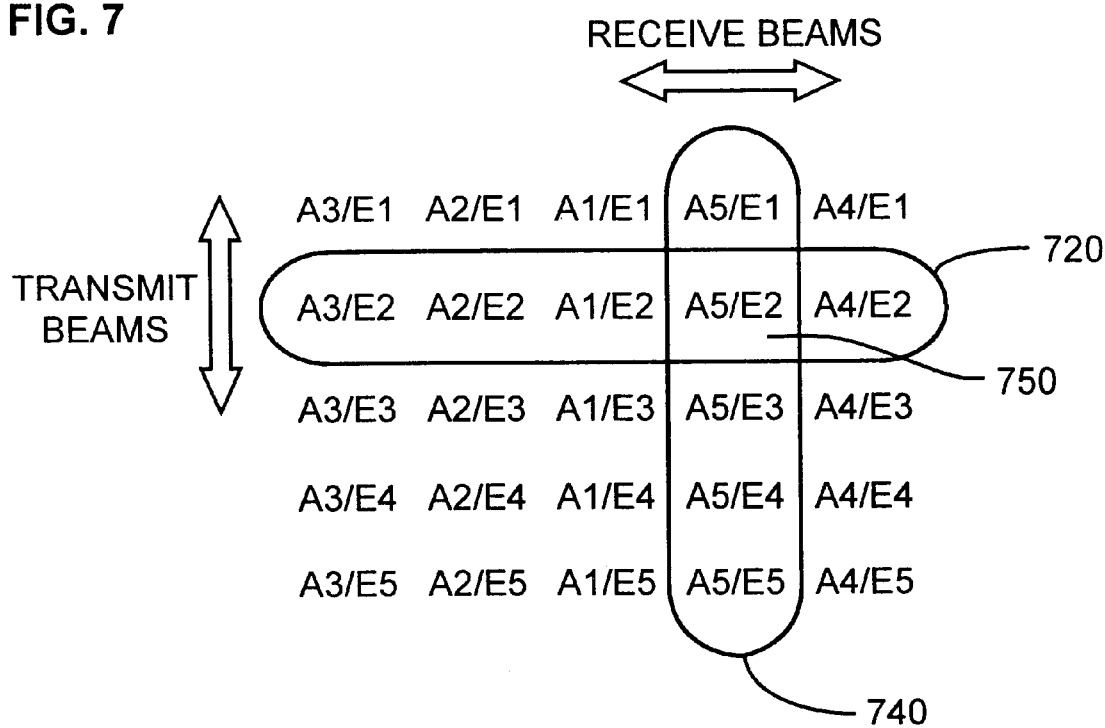
FIG. 7 illustrates the independent steering of beams from the two orthogonal sub-arrays in the transducer according to the invention.

By combining the beam profiles of the orthogonal apertures of the array 200 in elevation and azimuth, it is possible using the invention to generate 3D data in real-time. FIGS. 6 and 7 illustrate this technique: In the array 200, one of the orthogonal apertures is used to transmit to a depth where the beam width in elevation is wide and yet the orthogonal aperture offers a receive beam that is narrow. For example, 20 mm would be a typical target depth. Assume that the transmit aperture is in the elevation dimension. In receive, the aperture (here, the azimuth plane) orthogonal to the transmit aperture would be then used as the receive aperture, which will have a beam profile that is nearly identical to the transmit aperture, except that it will be oriented, that is, rotated, 90 degrees relative to the transmit aperture. The region where the transmit and receive beam profiles overlap is the region that will be scanned. In other words, the array transmits in one plane, but receives ("listens") along another, which is orthogonal to the first. In FIG. 7, this is the region labeled A5/E2.

Because the receive aperture can be electronically steered (using conventional phasing techniques) in the elevation dimension of the transmit aperture, multiple regions can be scanned simultaneously. In FIG. 7, the five regions A3/E2, A2/E2, A1/E2, A5/E2 and A4/E2 can all be received simultaneously using parallel receive processing. Note that, because the orientations of the transmit and receive beams (or dual transmit followed by dual receive beams) are at every time known to (indeed, set by) the ultrasound system, the system will always know which region is being imaged.

Next, the transmit aperture is focused to a new region at the same depth and the process is repeated. Finally, a grid of points (in FIG. 7, all the regions labeled Ai/Ej) at that depth can be scanned. The procedure can then be repeated at a different depth by changing the depth focus. By combining data at various depths, a volume of information can be obtained. The number of data points obtained at a specific depth is dependent on the beam width of the apertures. By decreasing the height of the transmit aperture, volumes at deeper depths can be interrogated using this technique.

The array 200 according to the invention offers superior array sensitivity when compared with other techniques in the prior art that are used to generate real-time 3D data. Typically, in the prior art, a 2D array has been used to generate 3D data. Unfortunately, a 2D array is typically a 64-by-64 grid of subelements, for a total of 4096 subelements. It is difficult and therefore expensive to connect 4096 subelements. Because of the possible size of the transducer, a subset of the subelements is therefore used in a sparse 2D array. Unfortunately, removing subelements decreases the overall sensitivity offered by a 2D array. Furthermore, to generate 3D images in real-time, a certain amount of parallelism is required, which further decreases array sensitivity.

Simulations of the array sensitivity according to the invention and a standard 2D array for various degrees of receive parallelism were conducted. These tests showed that the sensitivity of the array according to the invention exceeded that of conventional sparse arrays that had 64, 128, 256, 512, and 1024 transmit and receive subelements. Indeed, one advantage of the invention is that it has been shown in simulations to produce similar detail and contrast resolution as conventional probes, but with a much lower system count (number of elements). In the arrangement illustrated in FIG. 7, the array according to the invention also uses receive parallelism, with five receive beams generated for each transmit pulse for real-time 3D imaging. The simulations showed that the sensitivity of the array according to the invention continued to exceed that of the conventional array until the amount of receive parallelism was two and the number of transmit and receive elements in the sparse array was 1024. Moreover, the comparison did not take into effect the significant impedance mismatch that the 2D array elements have with the conventional transmit and receive electronics.

INTERLEAVED MULTI-DIMENSIONAL ARRAYS

Figure 9A:
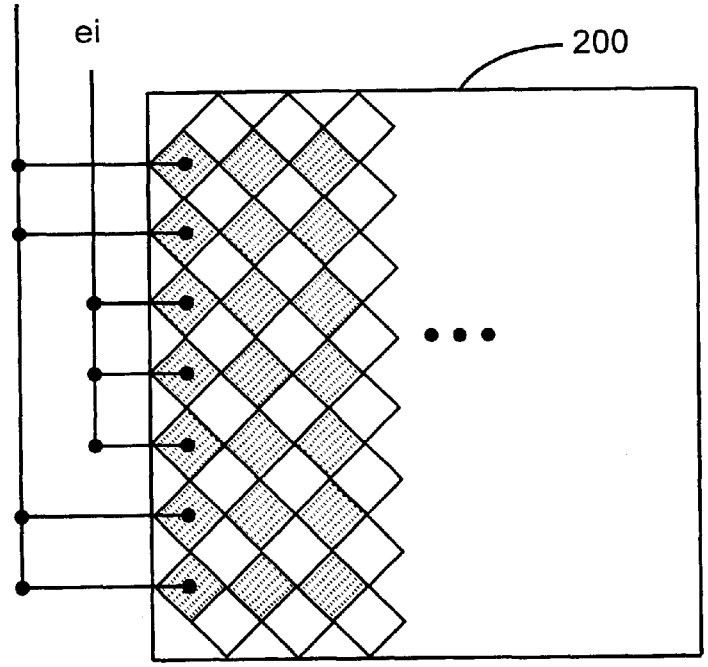
FIGS. 9A–9C illustrate an interconnection arrangement that configures the array according to the invention as a 1.5-D array.
Figure 9C:
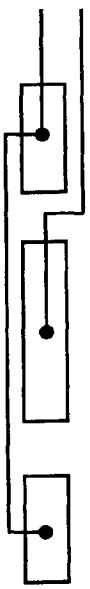
Figure 9B:
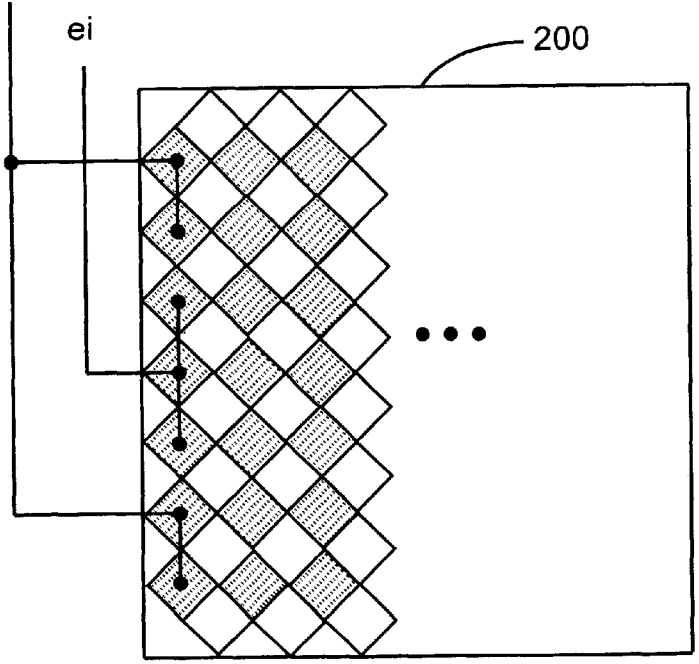

FIGS. 9A and 9B illustrate yet another interconnection arrangement. Here, not all adjacent subelements in each row or column are electrically connected; rather, groups of the subelements within the same column or row are electrically connected. FIGS. 9A and 9B show an array that defines two groups of electrically connected subelements within the same column: One group is connected with conductor eo and the other group is connected with conductor ei. This electrical connection is identical to the electrical connection used in expanding aperture arrays (1.25D) as well as arrays offering dynamic focusing in elevation (1.5D).

In an expanding aperture, the conductors ei and eo would connect to a switch that allows the two groups to be electrically connected in parallel or electrically independent. This would allow the aperture to be made larger or smaller depending on the imaging depth. Another technique is to keep the conductors separate, thereby allowing the groups to be phased differently (1.5D).

The number of groups in any given column may be greater than two. Furthermore, it is not a requirement to electrically connect the outer rows of the subelements together as shown for conductor eo. For example, the two subelements at the top of the column could be electrically separate from the bottom two subelements (1.75D). The subelements of the orthogonal aperture could also use this process (not necessary) to create two interleaved multi-dimensional transducers. FIG. 9C shows the equivalent array structure using elements of different length.

VOLUMETRIC CARDIAC MEASUREMENT

The calculation of cardiac output is important in determining cardiac ventricular or myocardial function. In order to calculate the volume of the left ventricle of the heart, conventional probes use an algorithm based on an equation termed the "method of discs." By calculating the volume of the left ventricle at different times (in particular, end diastole and end systole), the stroke volume of the heart is calculated. The method of discs for a 2-D image of the left ventricle involves the following steps: First, images of the left ventricle are obtained in the conventional manner, typically through an apical four-chamber or two-chamber view. Then, using any conventional input device, such as moving an overlayed display cursor with a mouse or trackball, the sonographer manually traces a boundary of the endocardium, usually starting from the mitral valve.

After the boundary has been completed, the system processor (or the sonographer herself) determines and draws in the display the longest line segment, starting from the middle of the mitral valve to the apical endocardium. This line is called the major long axis of the ventricle. Finally, line segments that are perpendicular to the ventricular long axis and whose ends intersect the walls of the endocardium are generated. This produces a dense group of rectangles covering the displayed area of the left ventricle. This method then assumes that each "slice" of the ventricle is circular, that is, that the ventricular cavity has a surface defined as a surface of revolution. The ventricular volume V is then calculated as follows:

$$V = \frac{1}{4} \sum_{all\ discs} \pi d^2 \Delta h$$

where d is the length of the line segment and $\Delta h$ is the thickness of each disc.

The major source of error with the method of discs is the assumption that the interior of the ventricular cavity is a surface of rotation. By obtaining two simultaneous orthogonal images using the invention, this error can be reduced. In this case, the sonographer or cardiologist first manually traces the endocardium using two preferably orthogonal B-mode images, which may be generated using the invention's two orthogonal imaging sub-arrays (with imaging planes 720 and 740). This provides two orthogonal cross-sectional views and measurements instead of one, yet can be done with a single array, simultaneously, with no need to reorient it.

Figure 10A:
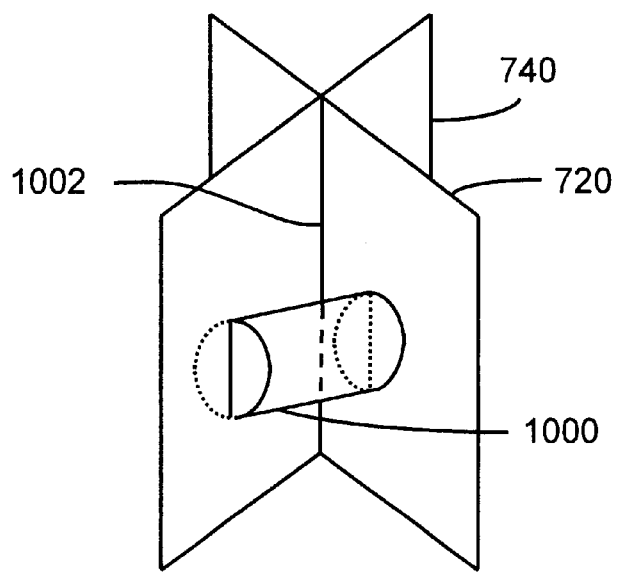
FIGS. 10A–10C illustrate the two simultaneous, orthogonal views of a 3-D object made possible by the invention.
Figure 10B:
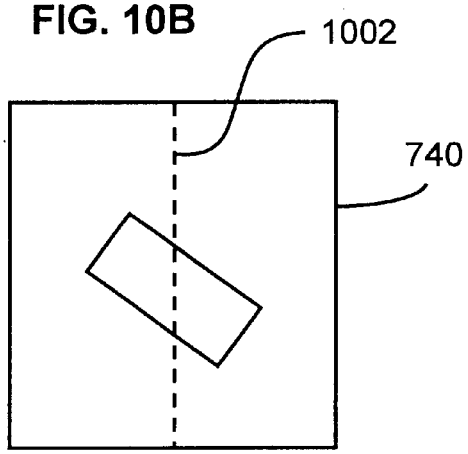
Figure 10C:
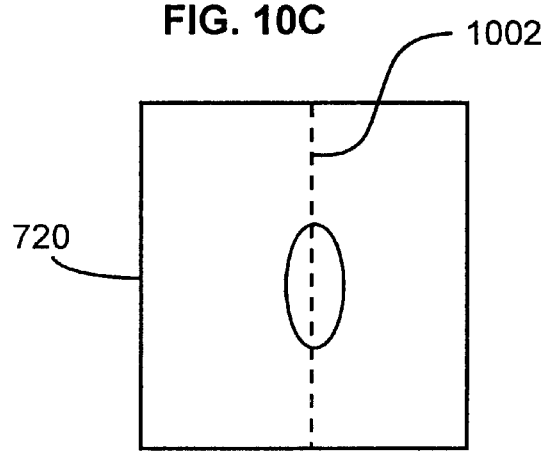

As an example of how the invention may be used to generate a volume measurement, assume that the region to be imaged and measured is a cylinder 1000. This is illustrated in FIGS. 10A–10C: FIG. 10A illustrates how the two imaging planes 720, 740 are generated through the volume 1000. FIGS. 10B and 10C show, respectively, the orthogonal B-mode images that would be generated in the two different planes. The dashed line 1002 shows the imaging line that is common to both B-mode images.

In use, the two images will be displayed simultaneously, for example, side-by-side on a conventional display, or on separated screens that the user switches between. The sonographer will trace the boundaries of the two images (rectangle and ellipse) as in conventional systems, for example, by moving a cursor around the boundaries.

Now consider how the volumetric measurement would proceed in the prior art. First, only one of the images (FIG. 10B or 10C) would be available. Second, the sonographer would select a long axis, and the system would then assume that the volume "slice" is a disc. The problem is, of course, that the assumption of a circular disc will usually be very inaccurate for a rectangular cross-section (FIG. 10B) and will be reasonably accurate for the elliptical section (FIG. 10C) only where the eccentricity of the ellipse is small.

Now instead of using a method of discs that assumes a circular disc, according to the method of this invention, the data in the two images are combined to generate a volume. For example, having the out-of-plane information in FIG. 10C allows elliptical discs to be generated.

The preferred method for combining the images according to this aspect of the invention is the known modified Simpson method, which uses two orthogonal views (apical 2- and 4-chamber) as described above. In a conventional probe, the apical 2- and 4-chamber views required by the modified Simpson method requires are obtained at separate times. Using the array according to the invention, both the 2- and the 4-chamber apical views can be obtained simultaneously. This not only decreases scanning time, but it also eliminates the need for EKG gating as with a conventional probe. Of course, other known algorithms that compute a volume from a sequence of orthogonal sectional views may also be used.

OTHER VOLUME MEASUREMENTS

The probe according to the invention also offers different modes of obtaining a 3D data set, namely, by either dragging or rocking the transducer in which the array 200 is mounted. Both methods, however, use one of the orthogonal planes to determine the distance traveled.

FIG. 11 diagrams the method of dragging the array, whose movement is indicated by the arrow 1100. In a conventional array, the sonographer must precisely control the speed of movement of the array over the patient during the generation of the 3D data set. The array according to the invention, however, allows the distance traveled to be uniquely determined, thereby greatly reducing this source of error.

In FIG. 11, three display frames (R1, R2, R3 and L1, L2, L3) are gathered from each plane (indicated as left L and right R) at times t1, t2, and t3, respectively. When gathering the frame at t2, frames R1 and R2 are spatially correlated to determine the distance the array traveled in the dragging direction. Any known method may be used to determine the distance based on spatial correlation. U.S. Pat. No. 5,582,173 (Li, Dec. 10, 1996, "System and method for 3-D medical imaging using 2-D scan data"), for example, describes a method that calculates distances based on speckle correlation.

At time t3, the process is repeated, and frames R2 and R3 are spatially correlated again to determine the distance traveled, which may vary based on the manual movement of the probe. This process continues until the full volume of the cylinder is generated using the planes L1, L2, L3, etc.

Another method for obtaining a 3D data set using the array according to the invention is by rocking the transducer, whose movement is indicated by the arrow 1200. This method is particularly useful in regions of the body where the acoustic window is limited, for example, by the lung or bones (skull and rib cage). FIG. 12 diagrams the rocking of the transducer, for which six B-mode images have been obtained at three different times t1, t2 and t3. As in the previous method, the plane on the right is used to determine the amount the transducer has been rocked. This eliminates errors that may be introduced by the sonographer when the transducer is manually rocked at different speeds. The B-mode planes on the left are aligned based on the amount of rotation, which will produce a fan-like volume.

DUAL FOCUS IN THE PREFERRED EMBODIMENT OF THE INVENTION

The lens 520 in the preferred embodiment of the invention is designed to improve the ability of the array to independently and simultaneously adjust the focus of the two apertures, that is, of the two orthogonal scan planes made possible by the invention. In order to better understand the lens used in the invention, it is helpful to recall the way in which conventional arrays focus. These methods are therefore reviewed here.

Figure 13A:
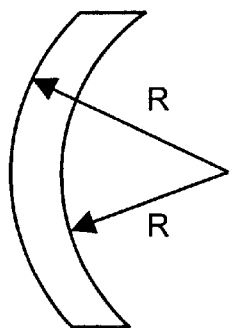
FIGS. 13A–13C illustrate different lens or ceramic geometries used in the array.

In conventional linear arrays, there are two primary methodologies for mechanically focusing the array in elevation where electronic delay control does not exist. According to the first method, the geometric focus is created by curving the ceramic. Typically, this is done by using a convex-concave ceramic as shown in FIG. 13A. The geometric focus is simply given by the following equation:

$$\frac{1}{f_g} = \frac{1}{R}$$

where the radius of curvature of the ceramic is equal to the geometric focus in elevation. This curvature only occurs in one dimension for a conventional linear array.

The second method uses a lens to bend the acoustic wave towards a geometric focus. Typically, the lens material has a sound velocity that is slower than water (1.5 mm/usec). The slower sound velocity of the lens gives it a characteristic convex shape. The equation governing the radius of curvature of the lens is given by the well-known lens-makers equation:

$$\frac{1}{s_0} + \frac{1}{s_1} = \left(\frac{v_{water}}{v_{lens}} - 1\right)\left(\frac{1}{R_1} - \frac{1}{R_2}\right) \quad \text{(EQ1)}$$

where $s_o$ is the distance to the object; $s_i$ is the distance to the image; $v_{lens}$ is the velocity of sound in the lens material; $v_{water}$ is the velocity in the water; $R_1$ is the radius of curvature of the first side of the lens; and $R_2$ is the radius of curvature of the second side of the lens.

Typically, the acoustic lens is curved only on the side that touches the patient ($R_2$); the other side is usually flat to allow mechanical connection to the transducer subelements. A flat surface implies the radius of curvature ($R_1$) is infinite. Moreover, the waves from the transducer are assumed to be collimated, which implies that $s_o$ is infinite. Equation EQ1 can therefore in this case be simplified to:

$$\frac{1}{f_g} = \left(\frac{v_{lens} - v_{water}}{v_{lens}}\right)\left(\frac{1}{R_2}\right)$$

Note that if $R_2$ is negative, then the lens is convex.

Figure 13B:
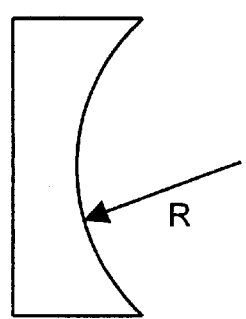
Figure 13C:
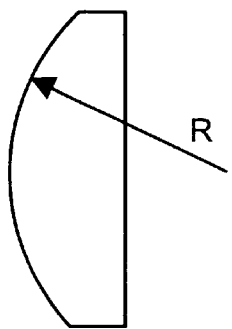

There are of course variations of these methods known in the prior art. For example, geometric focus may also be achieved by curving the ceramic (as opposed to just the lens) of the transducer. Furthermore, as with lenses, the ceramic could potentially be curved on only one side. These alternatives are illustrated in FIG. 13B (piano-concave) and FIG. 13C (convex-piano). Moreover, the array may combine a curved ceramic with a lens.

In the illustrated prior art arrangements, note that the radius of curvature appears only in the elevation dimension of the array. In this invention, however, mechanical focusing is needed and made possible in both the elevation and azimuth directions. The common aperture probe according to the invention therefore requires the lens 520 to focus or at least allow for focusing in both dimensions. According to the invention, the focus in one direction is done mechanically, whereas focus in the other is done electronically.

Figure 14A:
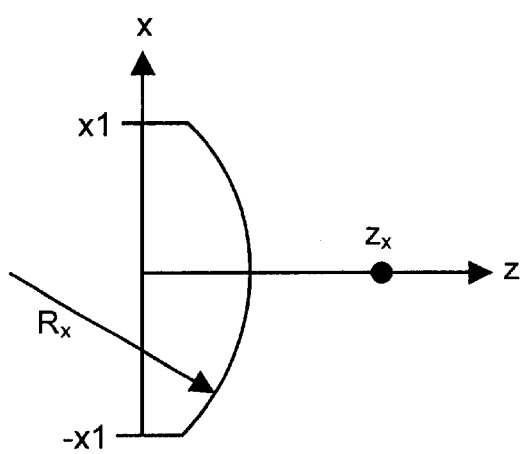
FIGS. 14A and 14B illustrate the geometry of a dual-focus lens used in the preferred embodiment of the invention.
Figure 14B:
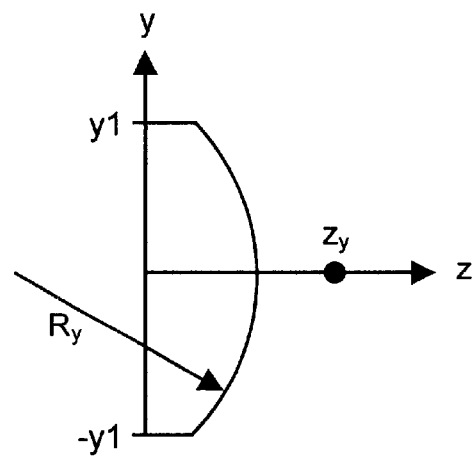

In order to accomplish this dual-focus ability, the lens 520 delay from the orthogonal aperture must be eliminated in the imaging plane dimension using electronic delays. The curvatures of the lens 520 in two dimensions should therefore be independent of one another for optimal performance. The equations for the radii of curvature of the two surfaces (in the x-dimension and y-dimension, respectively) of the common aperture probe lens according to the invention are therefore preferably equal to or at least substantially proportional to:

$$\frac{1}{f_{gx}} = \left(\frac{v_{lens} - v_{water}}{v_{lens}}\right)\left(\frac{1}{R_x}\right) \text{ and } \frac{1}{f_{gy}} = \left(\frac{v_{lens} - v_{water}}{v_{lens}}\right)\left(\frac{1}{R_y}\right)$$

where $f_{gx}$ is the geometric focus in the x-dimension; $R_x$ is the lens radius of curvature in the x-dimension; $f_{gy}$ is the geometric focus in the y-dimension; and $R_y$ is the lens radius of curvature in the y-dimension. FIGS. 14A and 14B show cross-sections of the lens in the x and y directions, respectively.

Let $\Delta = \Delta(x,y)$ = the thickness of the lens 520 at each point (x,y) given the coordinate system shown in FIGS. 14A and 14B. In the preferred embodiment of the invention, $\Delta$ is equal to or at least substantially proportional to:

$$\Delta = C - \frac{v_{lens}}{v_{water}}\left(\sqrt{z_x^2 + x^2} + \sqrt{z_y^2 + y^2}\right)$$

where C is a constant and $z_x$ and $z_y$ are the focal distances (assuming that the interrogation region within the patient lies in the positive z, that is, depth direction). This lens effectively places the following mechanical delay over the entire array:

$$\delta(x,y) = \frac{\Delta}{v_{lens}} = \delta_x(x) + \delta_y(y)$$

As the equation above shows, the lens delay is actually the sum of two functions, one a function of x and the other a function of y. Therefore, by knowing the lens geometry and the location of the element, the lens delay can be removed electronically using known techniques.

When the transducer is operated in the y-z plane (see FIG. 6), electronic delays $\delta_{ey}$ are applied to eliminate-any mechanical focusing in the y direction.

$$\delta_{ey}(y) = \delta_y(y)$$

Next, the standard delays $\chi X_y$ needed to produce the proper electronic focus in the y-z plane are applied. The actual delay over any element in the elevation aperture is therefore:

$$\theta(x,y) = \delta_x(x) + \delta_y(y) - \delta_{ey}(y) + \chi_y$$

This is identical to the delay of a conventional element. Similar techniques are used when operating in the x-z plane.

A second method according to the invention that may be used to achieve dual-direction focus is to design the ceramic from which the array subelements are diced to be convex-concave and thus curved ceramic in both the azimuth and elevation dimensions. The curving of the ceramic is thereby governed by the following equations:

$$\frac{1}{f_{gx}} = \frac{1}{R_x} \text{ and } \frac{1}{f_{gy}} = \frac{1}{R_y}$$

where $f_{gx}$ is the geometric focus in the x-dimension; $R_x$ is the ceramic's radius of curvature in the x-dimension; $f_{gy}$ is the geometric focus in the y-dimension; and $R_y$ is the ceramic's radius of curvature in the y-dimension.

As discussed above, conventional electronic delays should also be applied in order to remove any effects of the curved ceramic when operating in the x-z or y-z imaging plane. Given the discussion above of the two different methods (lens 520 design and ceramic curvature) for achieving dual-focus according to the invention, those skilled in the art of optics will also know how to apply other curvatures, as well as how to use a combination of a curved ceramic and a lens. It would also be possible to use a ceramic with a convex-piano or plano-concave shape as in the conventional case.

SYSTEM COMPONENTS

Figure 15:
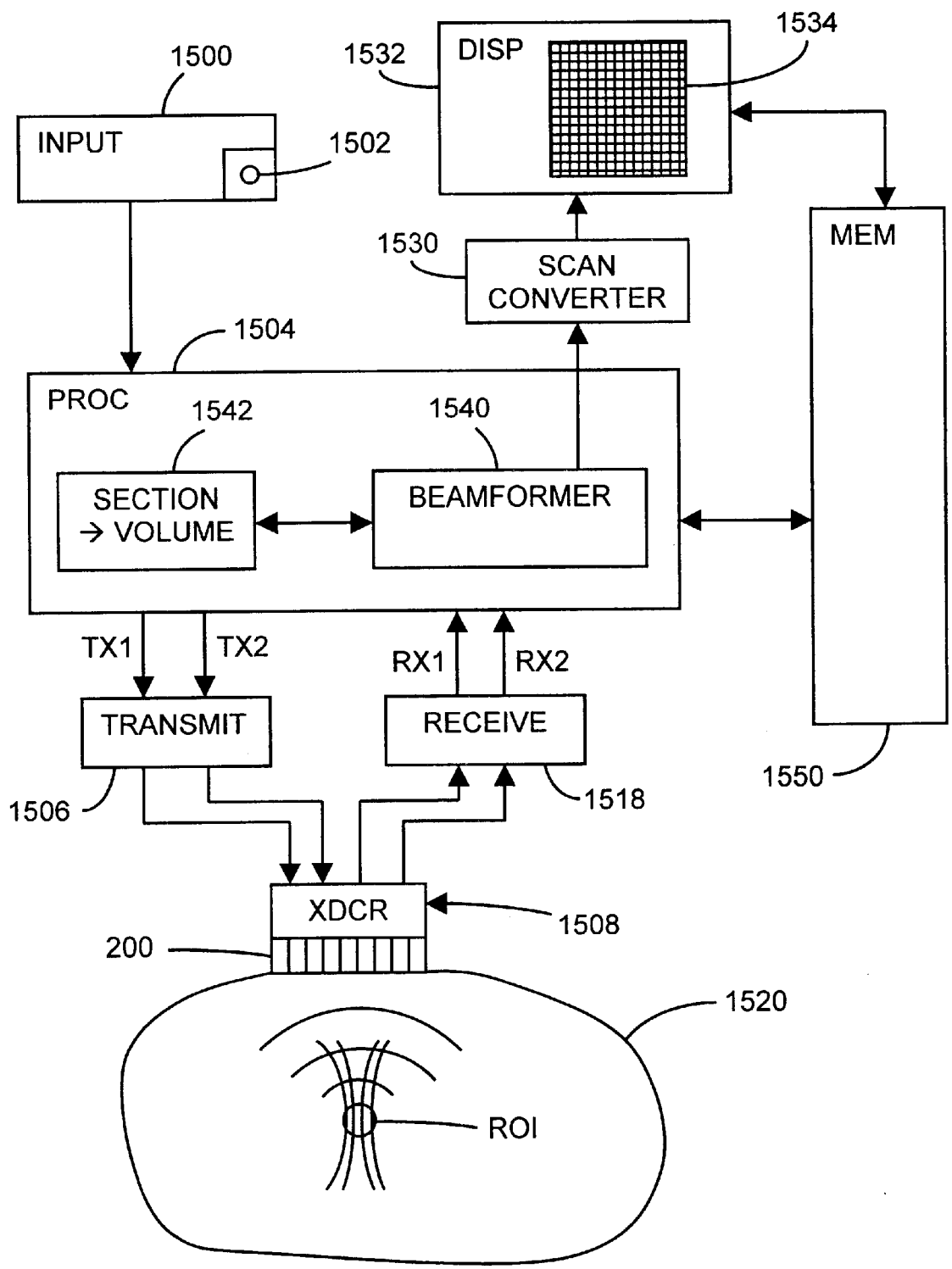
FIG. 15 is a block diagram that illustrates the main components of an ultrasonic imaging system according to the invention.

FIG. 15 illustrates the main components of an ultrasonic imaging system that is suitable for implementing the invention. The user enters various conventional scan parameters into an input unit 1500, which typically comprises conventional hardware input ports and any necessary drivers within an operating system and which typically includes such devices as a keyboard 1502, knobs, a mouse 1504, and/or buttons. Any of these devices may be used to position an on-screen cursor or similar marker in order, for example, to trace the periphery of the two images generated simultaneously in the embodiment of the invention illustrated in FIGS. 10A–12.

The input unit is connected to a processing system 1504, which will typically be an electrically connected and cooperating group of processors such as microprocessors and digital signal processors; the processing system may, however, also be implemented by a single processor as long as it is fast enough to handle the various tasks described below.

As in known systems, the processing system 1504 sets, adjusts, and monitors the operating parameters of a conventional transmission control circuit 1506. This control circuit 1506 generates and applies electrical control and driving signals to the ultrasonic probe, that is, transducer 1508, which includes the array 200. As is well known in the art, the piezoelectric subelements in the array generate ultrasonic waves when electrical signals of the proper frequency are applied to them.

In this invention, the two, preferably orthogonal, interleaved subarrays may be activated independently. Accordingly, the transmit control circuit, using conventional techniques, in this invention applies separate sets of control signals TX1, TX2 to the array 200 in order to activate, steer and focus the two orthogonal subarrays. Note that it would be possible using the invention to generate TX1 and TX2 so that they represent completely different waveforms; this would make it easier to distinguish these signals upon reception.

By placing the probe 1508 against the body of a patient, these ultrasonic waves enter a portion (the interrogation region, including the region of interest ROI) of the patient's body. By varying the phasing, amplitude, and timing of the driving signals TX1, TX2 in a conventional manner, the ultrasonic waves from the respective subarray's elements are formed into a respective transmit beam. Each beam will typically converge at a focal depth, beyond which it once again diverges. Each transmit beam is steered in the planes 720, 740 and focused in the depth D direction so as to concentrate the ultrasonic energy of the beam onto desired points within the ROI.

When any point in the interrogation region is insonified, the transducer is typically switched from the transmit mode to a receive mode. In the receive mode, ultrasonic energy from the waves created by the elements 1542 is reflected back (back-scattered) as a return echo signal to the array. As is well understood, the subelements in the array 200 convert the small mechanical vibrations caused by the echo signals into corresponding radio-frequency (RF) electrical signals. Amplification and other conventional signal conditioning is then applied to the return signals by a reception controller 1518. This processing includes, as needed, such known signal conditioning as time-gating, gain compensation, and diffraction compensation, in order to identify the echo signals that correspond to each scanned point in the interrogation region. The type of conventional signal processing needed will in general depend on the particular implementation of the invention and can be chosen using known design methods.

In the invention, two separate receive signals RX1, RX2 may be returned, one from each subarray, each corresponding to the return from a respective one of the transmit signals TX1, TX2. In the 3-D embodiment of the invention, as illustrated in FIG. 7, it is also possible to activate one of the subarrays using one set of transmit signals, say TX1, and then to receive, say, RX2, corresponding to the received signals of the orthogonal subarray, in order to isolate the echo return from particular points throughout a 3-D ROI.

Each subarray may, however, be activated and scanned simultaneously by respective transmit/receive pairs TX1/RX1, TX2/RX2, for example, to enable the dual-display volumetric imaging illustrated in FIGS. 10A–12.

The reception controller 1518, all or part of which is normally integrated into the processing system 1504 itself, converts the ultrasonic, radio-frequency (RF) return signals (typically on the order of a few to tens of megahertz) into lower frequency ranges for processing, and may also include analog-to-digital conversion circuitry. This is well known in the art of ultrasonic imaging. If not included in the reception controller 1518 itself, the processing system 1504 will include a beamformer 1540 that converts the conditioned return signals into corresponding return beams, each of which normally corresponds to the echo from a transmit beam.

The processing system 1504 will also include various hardware and software components necessary for performing the various calculations needed to create proper transmission control signals for steering either or both of the subarrays. These components may be designed using normal techniques. In particular, in the embodiment of the invention that enables volumetric measurement, the system according to the invention includes a software module 1542 for calculating a volume given the sequence of orthogonal 2-D sectional images as shown in FIGS. 10A–12.

In conventional B-mode scanning, each point within the interrogation region can then be represented as an intensity (brightness) value. The entire interrogation region can therefore be represented as a discretized pattern (matrix) of brightness or signal intensity values, which are stored as frame data in a memory 1550.

The interrogation region is normally not in the same shape as what the user wants to see displayed; even when it is, the digital acoustic intensity values that make up the frame data are normally not in a form suitable for driving a conventional gray-tone or color display directly. The acoustic intensity values for a selected 2-D sub-set (scan plane) are therefore applied to a conventional scan converter 1560, which converts the digital acoustic values into display intensity values that are suitable for use in driving a display device 1570.

The display device 1570 typically includes or is connected to a conventional display driver and includes a screen 1572 (for example, LED or CRT) that is divided into an X-Y (or polar) matrix or pattern of picture elements or "pixels" that make up an image that the user can view and interpret. Note that a displayed image element will often be made up of more than one pixel, but that this will depend on the relative resolutions of the scan and of the display. The invention does not require any particular relative resolution.

What is claimed is:

1. An ultrasonic imaging array comprising two independent, interleaved linear subarrays occupying a common array face, the subarrays being independently steerable and focusable in different imaging planes in which:
   each subarray comprises a plurality of elements and each element comprises at least one subelement;
   each subelement is quadrilateral and has a diagonal;
   adjacent subelements in each element are electrically connected via an interconnect portion; and
   the interconnect portion connecting each pair of adjacent subelements in each element is substantially linear and is aligned with the diagonals of the adjacent subelements.

2. An array as defined in claim 1, in which:
   the diagonals of all subelements in each element are aligned; and
   the interconnect electrically connecting the subelements in each element is linear over the extent of the array face.

3. An array as defined in claim 2, further comprising a multilayer flex circuit, in which:
   the interconnects for a first one of the subarrays are patterned as first linear traces onto a first separate layer of the flex circuit and extend to a first edge of the array face; and
   the interconnects for a second one of the subarrays are patterned as second linear traces onto a second separate layer of the flex circuit and extend to a second edge of the array face that is different from the first edge.

4. An array as defined in claim 3, further comprising a connector for each subarray, the connector for each subarray being connected to the interconnects of the respective subarray along the respective edge.

5. An array as defined in claim 2, in which:
   the subelements in each element are grouped into a plurality of groups, the groups in each element of each respective subarray having the same relative position within the subarray;
   the subelements in each group are electrically connected;
   whereby each subarray operates as a multidimensional array, with a dimension greater than one and less than two.

6. An array as defined in claim 5, in which a first group consists of a central plurality of subelements and a second group consists of the plurality of subelements located on either side of the first group.

7. An array as defined in claim 1, comprising first and second subelements, in which:
   the first subelements comprise a first one of the subarrays;
   the second subelements comprise a second one of the subarrays;
   edges of the subelements extend in a first and a second direction; and
   the first and second subelements are arranged in a pattern in which they alternate in both the first and second directions.

8. An array as defined in claim 1, in which each subarray constitutes an independent, unswitched aperture.

9. An array as defined in claim 1, further comprising an acoustic lens mounted over the array face, which defines a single, common aperture, in which:
   each subarray comprises a plurality of elements;
   the elements in a first one of the subarrays extend in an azimuth direction and the elements in a second one of the subarrays extend in an elevation direction, which is orthogonal to the azimuth direction; and
   the lens is curved in both the azimuth and elevation directions, whereby the subarrays are independently focusable.

10. An array as defined in claim 9, in which curvatures of the lens have radii substantially proportional to the following:

$$\frac{1}{f_{gx}} = \left(\frac{v_{lens} - v_{water}}{v_{lens}}\right)\left(\frac{1}{R_x}\right) \text{ and } \frac{1}{f_{gy}} = \left(\frac{v_{lens} - v_{water}}{v_{lens}}\right)\left(\frac{1}{R_y}\right)$$

where $f_{gx}$ is the geometric focus in the azimuth-dimension; $R_x$ is the lens radius of curvature in the azimuth-dimension; $f_{gy}$ is the geometric focus in the elevation-dimension; $R_y$ is the lens radius of curvature in the elevation-dimension; $v_{lens}$ is the velocity of sound in the lens; and $v_{water}$ is the velocity in water.

11. An array as defined in claim 10, in which the lens has a thickness substantially proportional to the following:

$$\Delta = C - \frac{V_{lens}}{V_{water}}\left(\sqrt{z_x^2 + x^2} + \sqrt{z_y^2 + y^2}\right)$$

where $\Delta=\Delta(x,y)$ is the thickness of the lens at each point $(x,y)$, where x is an azimuth coordinate and y is an elevation coordinate; C is a constant; and $z_x$ and $z_y$ are focal distances in a depth direction that is orthogonal to the azimuth and elevation directions.

12. An array as in claim 1, in which the subelements are diced from ceramic and are convex-concave, that is, curved in both the first and second dimensions, the first and second directions being orthogonal, whereby the subarrays may be focused in both the first and second directions.

13. A method for imaging a region of interest of a body using ultrasound, in which the, region of interest includes a body structure, comprising:
  activating and independently steering in different imaging planes interleaved linear subarrays of ultrasound-generating elements occupying a common face of an ultrasound array;
  receiving echo signals from within the region of interest along the different imaging planes;
  generating from the received echo signals and simultaneously displaying for a user two orthogonal cross-sectional B-mode images of the region of interest;
  moving the array to a plurality of positions;
  at each position, tracing a periphery of the body structure as displayed in a first one of the orthogonal cross-sectional B-mode images;
  measuring distance of movement of the array as a function of sequentially generated second ones of the B-mode images, which are orthogonal to the first B-mode images; and
  calculating a volume of the structure as a function of the products of areas within the traced periphery and the corresponding measured distances, summed over all the positions of the array.

14. An ultrasonic imaging system comprising:
  an ultrasound transducer having two independent, interleaved linear subarrays occupying a common array face;
  transmission control means for activating and independently steering the subarrays in different imaging planes;
  reception means for receiving echo signals from insonified points within a region of interest and for converting the received echo signals into a predetermined display format; and
  display means for displaying the converted echo signals in which:
    each subarray comprises a plurality of elements and each element comprises at least one subelement;
    each subelement is quadrilateral and has a diagonal;
    adjacent subelements in each element are electrically connected via an interconnect portion; and
    the interconnect portion connecting each pair of adjacent subelements in each element is substantially linear and is aligned with the diagonals of the adjacent subelements.

15. A system as in claim 14, further comprising:
  processing means for independently generating two orthogonal cross-sectional B-mode images of a region of interest;
  the display means being further provided for simultaneously displaying the two orthogonal cross-sectional B-mode images for a user.

16. A system as in claim 15, further comprising:
  input means maneuverable by the user for tracing a periphery of a body structure as displayed in a first one of the orthogonal cross-sectional B-mode images;
  volume calculation means for measuring distance of movement of the array as a function of sequentially generated second ones of the B-mode images, which are orthogonal to the first B-mode images and for calculating a volume of the structure as a function of the products of areas within the traced periphery and the corresponding measured distances, summed over a plurality of positions of the array.

17. An ultrasonic imaging array comprising two independent, interleaved linear subarrays occupying a common array face, in which:
  each subarray comprises a plurality of elements and each element comprises at least one subelement;
  each subelement is quadrilateral and has a diagonal;
  adjacent subelements in each element are electrically connected via an interconnect portion;
  the interconnect portion connecting each pair of adjacent subelements in each element is substantially linear and is aligned with the diagonals of the adjacent subelements;
  the diagonals of all subelements in each element are aligned;
  the first subelements comprise a first one of the subarrays;
  the second subelements comprise a second one of the subarrays;
  edges of the subelements extend in a first and a second direction; and
  the first and second subelements are arranged in a pattern in which they alternate in both the first and second directions; and
  the interconnect electrically connecting the subelements in each element is linear over the extent of the array face;
  whereby each subarray constitutes an independent, unswitched aperture, the subarrays being independently steerable and focusable in different imaging planes.

18. An ultrasonic system for volumetric measurement comprising:
  an ultrasound transducer having two independent, interleaved linear subarrays occupying a common array face;
  transmission control means for independently activating and independently steering the subarrays in different imaging planes;
  reception means for receiving echo signals from insonified points within a region of interest and for converting the received echo signals into a predetermined display format;
  processing means for independently generating two orthogonal cross-sectional B-mode images of a region of interest;
  display means for displaying the converted echo signals and for simultaneously displaying the two orthogonal cross-sectional B-mode images for a user;
  input means maneuverable by the user for tracing a periphery of a body structure as displayed in a first one of the orthogonal cross-sectional B-mode images;
  volume calculation means for measuring distance of movement of the array as a function of sequentially generated second ones of the B-mode images and for calculating a volume of the structure as a function of the products of areas within the traced periphery and the corresponding measured distances, summed over a plurality of positions of the array.

19. An acoustic lens for an ultrasound array, which has elements extending both an azimuth direction an elevation direction, which is orthogonal to the azimuth direction, the lens being curved in both the azimuth and elevation directions;

in which curvatures of the lens have radii substantially proportional to the following:

$$\frac{1}{f_{gx}} = \left(\frac{v_{lens} - v_{water}}{v_{lens}}\right)\left(\frac{1}{R_x}\right) \text{ and } \frac{1}{f_{gy}} = \left(\frac{v_{lens} - v_{water}}{v_{lens}}\right)\left(\frac{1}{R_y}\right)$$

where $f_{gx}$ is the geometric focus in the azimuth-dimension; $R_x$ is the lens radius of curvature in the azimuth-dimension; $f_{gy}$ is the geometric focus in the elevation-dimension; $R_y$ is the lens radius of curvature in the elevation-dimension; $V_{lens}$ is the velocity of sound in the lens; and $v_{water}$ is the velocity in water.

20. A lens as defined in claim 19, in which the lens has a thickness substantially proportional to the following:

$$\Delta = C - \frac{v_{lens}}{v_{water}}\left(\sqrt{z_x^2 + x^2} + \sqrt{z_y^2 + y^2}\right)$$

where $\Delta = \Delta(x,y)$ is the thickness of the lens at each point (x,y), where x is an azimuth coordinate and is an elevation coordinate; C is a constant; and $Z_x$ and $z_y$ are focal distances in a depth direction that is orthogonal to the azimuth and elevation directions.

* * * * *